(12) United States Patent
Kuebler et al.

(10) Patent No.: US 8,891,164 B2
(45) Date of Patent: Nov. 18, 2014

(54) SYSTEM FOR WAVEFRONT ANALYSIS AND OPTICAL SYSTEM HAVING A MICROSCOPE AND A SYSTEM FOR WAVEFRONT ANALYSIS

(75) Inventors: Christoph Kuebler, Oberkochen (DE); Daniel Kolster, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 179 days.

(21) Appl. No.: 13/399,961

(22) Filed: Feb. 17, 2012

(65) Prior Publication Data
US 2012/0147460 A1 Jun. 14, 2012

Related U.S. Application Data

(63) Continuation of application No. PCT/EP2010/005073, filed on Aug. 18, 2010.

(60) Provisional application No. 61/234,816, filed on Aug. 18, 2009.

(30) Foreign Application Priority Data

Aug. 18, 2009 (DE) .......................... 10 2009 037 841

(51) Int. Cl.
| | | |
|---|---|---|
| *G02B 21/06* | (2006.01) | |
| *A61B 3/13* | (2006.01) | |
| *G02B 21/00* | (2006.01) | |
| *G01J 9/00* | (2006.01) | |
| *G02B 21/22* | (2006.01) | |
| *G02B 21/24* | (2006.01) | |

(52) U.S. Cl.
CPC . *G02B 21/00* (2013.01); *A61B 3/13* (2013.01); *G01J 9/00* (2013.01); *G02B 21/22* (2013.01); *G02B 21/24* (2013.01)
USPC .......................................................... 359/389

(58) Field of Classification Search
USPC ......... 359/389, 362, 368, 363, 372–376, 385, 359/388; 250/201.1, 201.9; 351/205, 351/209–212
See application file for complete search history.

(56) References Cited

U.S. PATENT DOCUMENTS

| | | |
|---|---|---|
| 5,349,468 A | 9/1994 | Rathbone et al. |
| 6,582,079 B2 | 6/2003 | Levine |

(Continued)

FOREIGN PATENT DOCUMENTS

| | | |
|---|---|---|
| DE | 44 13 920 B4 | 7/2004 |
| DE | 10 2005 031 496 A1 | 1/2007 |

(Continued)

OTHER PUBLICATIONS

International Search Report and Written Opinion of the International Searching Authority for related International Application No. PCT/EP2010/005073 mailed on Feb. 25, 2011, 13 pages.

(Continued)

*Primary Examiner* — Stephone B Allen
*Assistant Examiner* — Tamara Y Washington
(74) *Attorney, Agent, or Firm* — Patent Portfolio Builders PLLC

(57) ABSTRACT

An optical system, comprising a microscope housing having a coupling opening for a detachable coupling of an objective lens of the optical system such that the objective lens is arranged in a microscope beam path of the optical system for imaging an object region of the objective lens. The optical system further comprises an assembly. The assembly comprises an assembly housing having a coupling element for the detachable coupling of the coupling element and the coupling opening of the microscope housing; a wavefront analysis system, which provides a wavefront beam path; and a beam splitter, which is arranged in the wavefront beam path. The objective lens, the beam splitter and the wavefront analysis system are arranged such that during the coupling of the coupling opening and the coupling element, the objective lens is arranged in the microscope beam path and the object region is arranged in the wavefront beam path.

50 Claims, 6 Drawing Sheets

(56) References Cited

U.S. PATENT DOCUMENTS

| | | | |
|---|---|---|---|
| 7,295,371 | B1 | 11/2007 | Sedlmayr |
| 7,463,414 | B2 * | 12/2008 | Storz et al. ............... 359/379 |
| 7,845,798 | B2 | 12/2010 | Kuebler et al. |
| 2005/0024720 | A1 * | 2/2005 | Cartlidge et al. ............. 359/368 |
| 2005/0241653 | A1 | 11/2005 | Van Heugten et al. |
| 2006/0012872 | A1 * | 1/2006 | Hayashi et al. ............... 359/386 |
| 2006/0126018 | A1 | 6/2006 | Liang |
| 2008/0062384 | A1 | 3/2008 | Rombach |
| 2008/0297890 | A1 * | 12/2008 | Natori et al. ................. 359/372 |

FOREIGN PATENT DOCUMENTS

| | | |
|---|---|---|
| DE | 10 2007 042 571 A1 | 4/2008 |
| DE | 10 2008 047 400 A1 | 4/2010 |
| DE | 102008062908 A1 * | 6/2010 |
| WO | WO 2011/020606 A2 | 2/2011 |

OTHER PUBLICATIONS

Office Action in the counterpart German Application No. 10 2009 037 541.3, dated Apr. 9, 2010, 15 pages.

Josef F. Bille et al., "The Development of Wavefront Technology and its Application to Ophthalmology"; Aberration-Free Refractive Surgery: New Frontiers in Vision, 2. Enlarged Edition, Springer, 2004, chapter 1, 11 pages.

Maria Regina Chalita et al., "Shack-Hartmann Aberrometry: Historical Principles and Clinical Applications", Wavefront Customized Visual Correction, The Quest for Super Vision II, SLACK, 2004, chapter 15, 3 pages.

Geunyoung Yoon et al., "Optimizing the Shack-Hartmann Wavefront Sensor", Wavefront Customized Visual Correction, The Quest for Super Vision II, SLACK, 2004, chapter 16, 6 pages.

G. Smith et al., "The Eye and Visual Optical Instruments", Cambridge, 1997, chapter 31, 12 pages.

User Manual WASCA Analyzer, Carl Zeiss Meditec AG, Jena, 2005, 96 pages.

K. K. Sharma, "Polarization of Light Waves", Optics Principles and Application, Academic Press, 2006, chapter 3, 19 pages.

www.fourieroptics.org.uk/jones.html.pdf, downloaded from internet on Apr. 5, 2010, 4 pages.

Austin Roorda, "A Review of Basic Wavefront Optics", Wavefront Customized Visual Correction, The Quest for Super Vision II, SLACK, 2004, chapter 2, 9 pages.

Larry N. Thibos et al., "Assessment of Optical Quality", Wavefront Customized Visual Correction, The Quest for Super Vision II, SLACK, 2004, chapter 6, 9 pages.

* cited by examiner

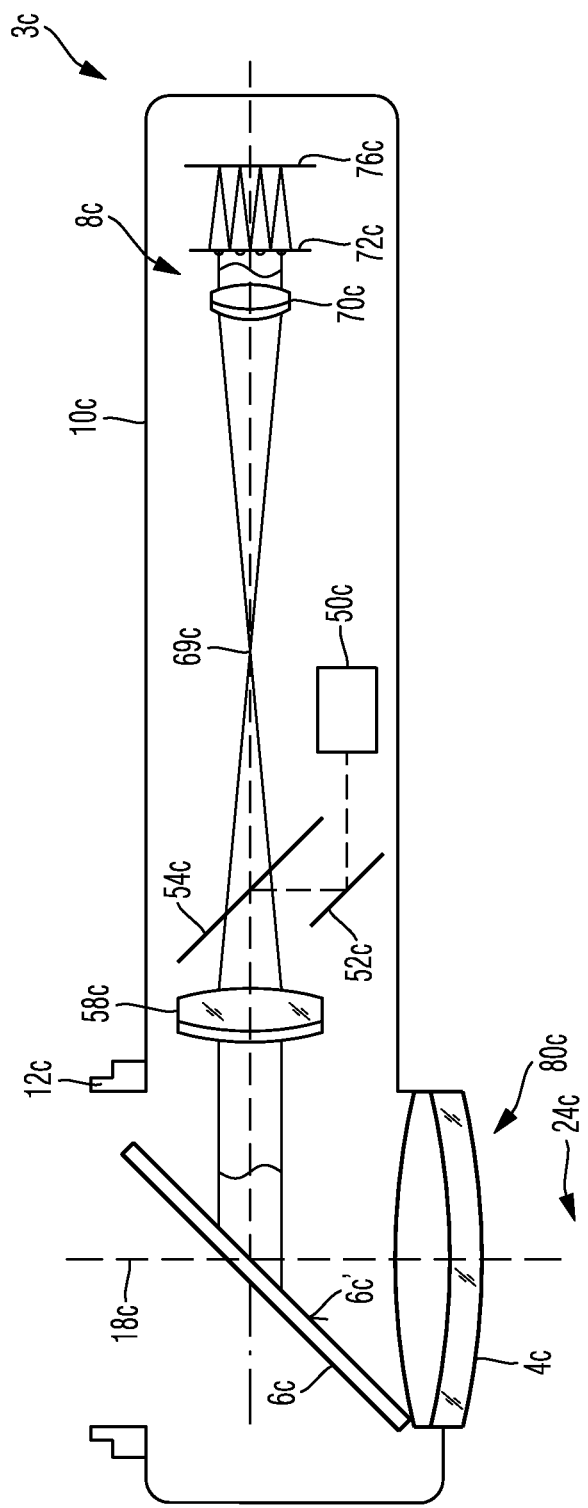

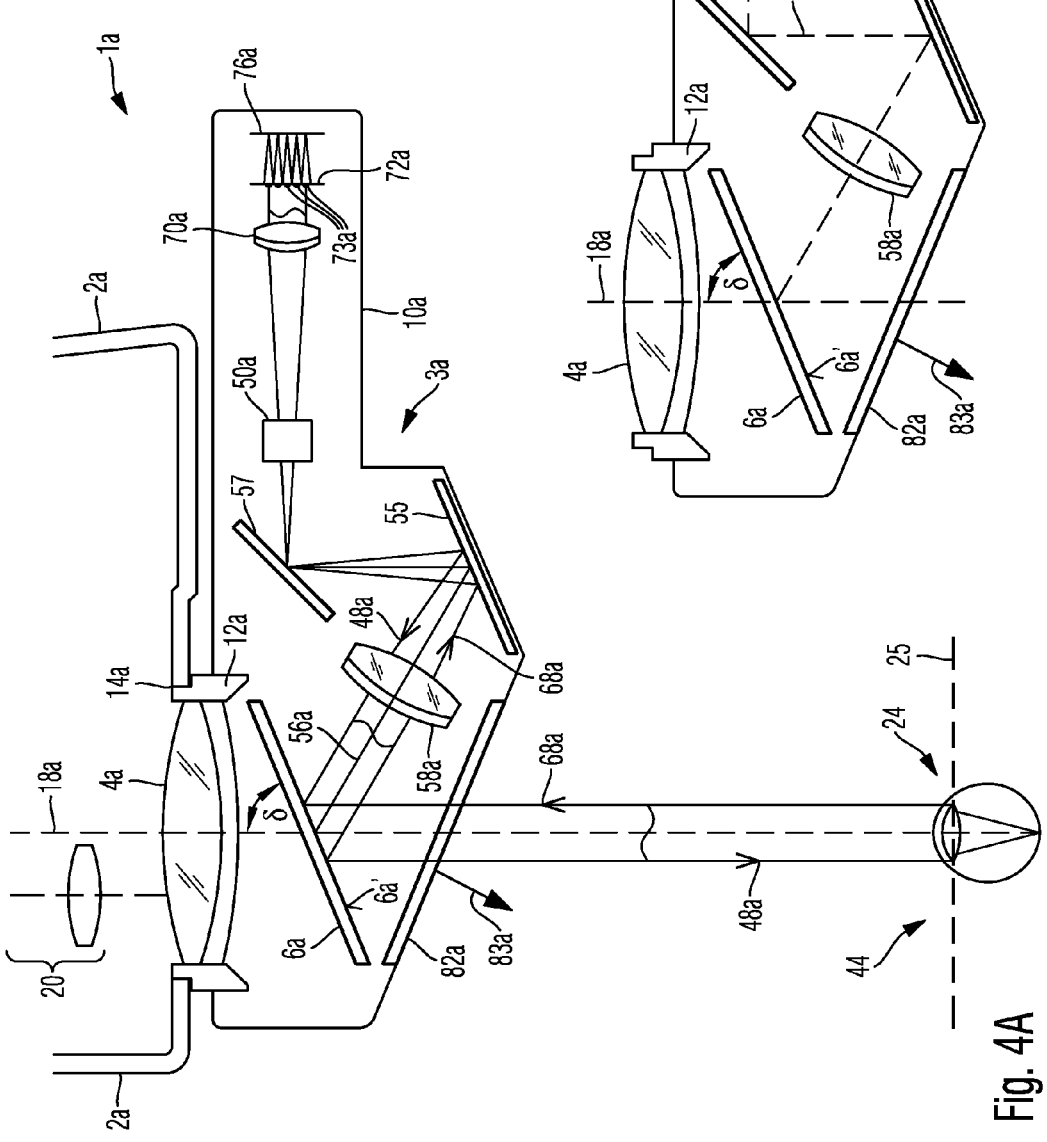

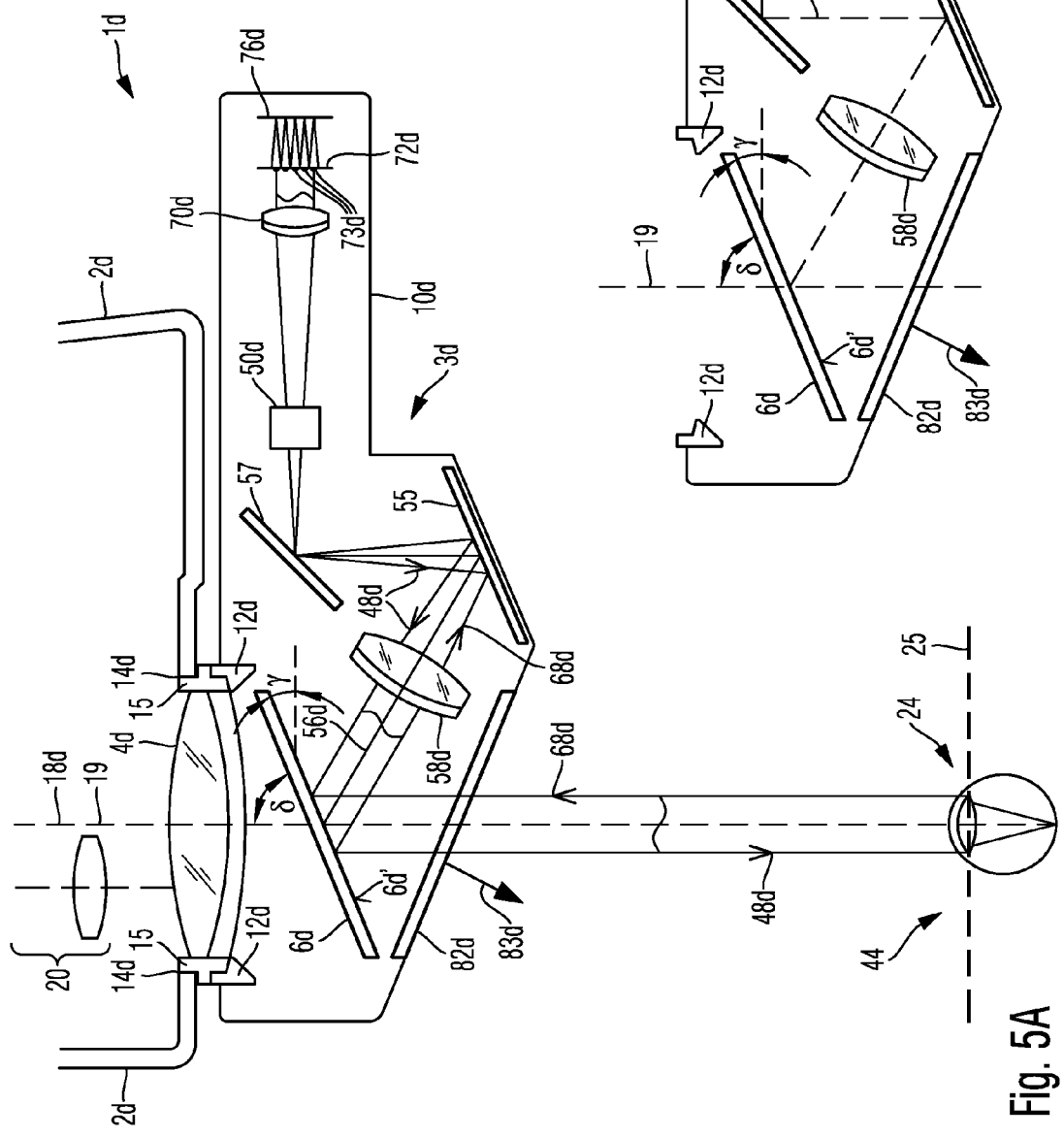

SYSTEM FOR WAVEFRONT ANALYSIS AND OPTICAL SYSTEM HAVING A MICROSCOPE AND A SYSTEM FOR WAVEFRONT ANALYSIS

CROSS-REFERENCES TO RELATED APPLICATIONS

The present application claims priority to and is a continuation of International Patent Application PCT/EP2010/005073, which claims priority to DE Patent Application No. 10 2009 037 841.3, filed Aug. 18, 2009 in Germany, entitled "SYSTEM FOR WAVEFRONT ANALYSIS AND OPTICAL SYSTEM HAVING A MICROSCOPE AND A SYSTEM FOR WAVEFRONT ANALYSIS" and to U.S. Provisional Patent Application No. 61/234,816, filed Aug. 18, 2009, entitled "SYSTEM FOR WAVEFRONT ANALYSIS AND OPTICAL SYSTEM HAVING A MICROSCOPE AND A SYSTEM FOR WAVEFRONT ANALYSIS". The present application is related to U.S. patent application Ser. No. 12/644,746 filed on Dec. 22, 2009, now U.S. Pat. No. 7,845,798 issued on Dec. 7, 2010. The contents of these applications are hereby incorporated by reference.

FIELD OF THE INVENTION

The present invention relates to a system for wavefront analysis and to an optical system comprising a microscope and a system for wavefront analysis. In particular, the present invention relates to an optical system wherein an assembly having an objective lens and a wavefront analysis system, can be detachably coupled to a microscope housing for optically image the object region and for analyzing wavefronts, which emanate from the object region.

BACKGROUND OF THE INVENTION

Microscopes are used for a variety of objects and in different fields. For example, surgical microscopes are used in the field of ophthalmic surgery. During a cataract surgery it is of interest to determine the optical properties of the eye before, during or after the surgical operation. Optical properties of the eye, are often determined by using a wavefront analysis system.

It has shown, that commonly used microscopes are insufficient for performing wavefront analysis.

It is an object to provide an optical system to efficiently perform optical microscopy and wavefront analysis.

SUMMARY OF THE INVENTION

According to an embodiment, there is provided an optical system, comprising: a microscope housing having a coupling opening for a detachable coupling an objective lens of the optical system such that the objective lens is arranged in a microscope beam path of the optical system for imaging an object region of the objective lens; and an assembly, which comprises an assembly housing having a coupling element for the detachable coupling of the coupling element and the coupling opening of the microscope housing; the objective lens; a wavefront analysis system, which provides a wavefront beam path; and a beam splitter, which is arranged in the wavefront beam path, wherein the objective lens, the beam splitter and the wavefront analysis system are arranged such and the coupling element and the coupling opening are designed such that during the coupling of the coupling opening and the coupling element the objective lens is arranged in the microscope beam path and the object region is arranged in the wavefront beam path.

The detachable coupling may be defined as a state in which the coupling element and the coupling opening are coupled. The coupling element and the coupling opening may be decoupled when they are in the coupled state.

The housing of the microscope and/or the housing of the assembly may be designed as a rack, case, frame or a combination of these. They may be designed integrally. Alternatively, the housing of the microscope and/or the housing of the assembly consist of a plurality of parts, which are mounted together, for example by using detachable or non-detachable fixing devices, such as screws, rivets, welding seams or the like. The microscope housing and the housing of the assembly serve to provide a basic structure at which further components such as lenses or mirrors may be supported.

The housing of the microscope has a coupling opening in the region of the beam path of the microscope. An objective lens is coupleable to the coupling opening of the microscope. In the coupled state, i.e. after the objective lens has been coupled to the coupling opening, the objective lens is arranged in the beam path of the microscope such that an object region is imageable by the microscope. The coupling opening may comprise a structure, wherein portions of the structure are complementary to a structure of the coupling element of the assembly housing. Thereby, the coupling opening and the coupling element may be detachably engaged with each other (i.e. they may later be separated again).

The coupling opening and/or the coupling element may further comprise a locking element for securing the coupling of the coupling opening and the coupling element against unintentional disengagement. The coupling opening may comprise a thread, for example a female thread and the coupling element may also comprise a thread, for example a male thread. An extent of the coupling opening may be such that the coupling element is at least partly accommodatable in the coupling opening. For example, the coupling element may at least partly be pushed into or screwed into the coupling opening or may be connected with the coupling opening by a combination of a rotary and plug-in movement. The coupling opening and/or the coupling element may comprise a catch.

Instead of coupling the coupling element of the assembly housing directly to the coupling opening, the coupling of the coupling opening and the coupling element may be performed via an adapter, which is arranged between the coupling opening and the coupling element. A portion of the adapter may comprise a complementary structure to the structure of the coupling opening. A second portion of the adapter may comprise a complementary structure to the coupling element. The adapter may be coupled to at least a portion of the coupling opening and/or the coupling element through a screw catch and/or bayonet catch.

The housing of the assembly may be designed as a case, a rack, a frame, as a mechanical holding structure or a combination of these, for holding the objective lens, the wavefront analysis system and the beam splitter. Additionally, further elements of the assembly may be attached to the housing of the assembly. Through a coupling of the coupling element of the housing of the assembly to the coupling opening of the housing of the microscope, the assembly housing, the objective lens, the beam splitter and the wavefront analysis system may be coupled to the microscope housing.

Thereby, the objective lens of the assembly is arranged in the microscope beam path such that the object region is imageable by the microscope. Also thereby, the object region is arranged in the wavefront beam path. Thereby, it is possible that by coupling the coupling opening and coupling element, the assembly is arranged relative to the housing of the microscope such that optical microscopy of the object region may be performed as well as an analysis of wavefronts, which are emitted from an object, which is arranged in the object region or wavefronts, which traverse the object region.

The objective lens may comprise a lens or a group of lenses and may have a positive optical refractive power. The objective lens may be the optical element of the optical system, which has the greatest cross-sectional extent of all optical elements of the optical system. The cross-sectional extent may be a cross-sectional diameter. A cross-sectional diameter of the objective lens may be in the range of 40 mm to 60 mm. A focal length of the objective lens may be in the range of 150 mm to 250 mm.

A wavefront analysis system may be defined as an optical system for characterizing a shape of a wavefront. The wavefront analysis system may comprise a wavefront sensor. The wavefront sensor may for example be a Hartmann-Shack sensor. A Hartmann-Shack sensor may comprise an array of microlenses which have a common focal plane. In the common focal plane, there may be arranged a position sensitive light detector. The shape of a wavefront which is incident on the array of microlenses may be determined by determining the local inclination of the wavefront in each of the regions of the individual microlenses. In order to measure the optical properties of a human eye, a spot as small as possible is generated on the retina of the human eye. From this punctiform illumination spot, a nearly spherical wave is emitted which traverses the vitreous body, the lens and the cornea and leaves the human eye. The shape of the wavefront is varied when optical interfaces of the human eye are traversed. This leads to a deviation of the wavefront from a plane wavefront in the case of ametropia. The ametropia may in particular comprise myopia, hyperopia and/or astigmatism. These deviations from a plane wavefront may be represented by a local deviation of the propagation direction from a propagation direction of a plane wavefront. This deviation of the propagation direction may be measured by the Hartmann-Shack sensor.

Additionally or alternatively to the above described array of microlenses, the wavefront analysis system may comprise computer, which is configured such that a hologram is calculable for determining a shape of a wavefront.

The wavefront beam path may be defined by an arrangement of optical components of the wavefront analysis system and the arrangement of the beam splitter, at least within a spatial region, which is defined by the assembly housing. A part of the wavefront beam path which is located outside of the spatial region of the assembly housing may be defined by an arrangement of the beam splitter and an arrangement of the entry/exit region of the assembly through which light entries into or exits from the assembly. Optical elements such as lenses of the wavefront analysis system may define a distance of a region from the assembly, wherein wavefronts which emanate from this region are characterizable by the wavefront analysis system. In particular, during the coupling of the coupling opening and the coupling element, the object region may be imageable onto a detection surface of the wavefront sensor. The detection surface of the wavefront sensor may be the array of microlenses. For example, a plane in the object region and a plane defined by the detection surface of the wavefront sensor may form optically conjugate planes. The microscope beam path is configured such that the object region is imageable onto the retina of an observer. The microscope beam path traverses the objective lens. The microscope beam path may traverse further lenses, such as a zoom system and/or an eyepiece, which may be supported at the microscope housing. Additionally or alternatively, the object region may be imaged along the microscope beam path of the microscope onto a sensor of a camera. For example, a semi-transparent mirror may be placed into the microscope beam path between the object region and the eyepieces, which decouples light, wherein the decoupled light is imaged onto the sensor of the camera.

The objective lens, the beam splitter and the wavefront analysis system are supported at the housing of the assembly. Thereby, it is possible that an exact relative and permanent position of these elements is ensured. For example, the assembly may be mounted to the microscope housing without having to adjust the position of the objective lens, the beam splitter and the wave front analysis relative to each other. Thereby, it is possible to quickly mount the assembly to the microscope, even for an unexperienced user. Also, the reliability of the operation of the wavefront analysis system is ensured, since a mounting or dismounting operation does not affect the imaging performance of the optical system.

In particular, one or more axes of a microscope beam path and an axis of the wavefront beam path can be adjusted with a high precision. The axis or axes of the microscope beam path may be defined in particular by an optical axis of the objective lens, and the axis of the wavefront beam path may be defined in particular by optical components of the wavefront analysis system. For example, an alignment or an intersection of the axis or axes of the microscope beam path and the axis of the wavefront beam path may adjusted. An intersection may for example be adjusted by an adjustment of a position of the beam splitter.

The objective lens, the beam splitter and the wavefront analysis system are adjustable in their position relative to each other.

Thereby, it is possible that an adjustment of a position of the objective lens, a position of the beam splitter and a position of the wavefront analysis system relative to each other is performed. Furthermore, it is possible that the position of the objective lens, the position of the beam splitter and the position of the wavefront analysis system is adjustable when the assembly is dismounted from the microscope housing. Thereby, an adjustment operation may be more easily and accurately carried out.

According to a further embodiment, further optical elements of the wavefront analysis system, such as lenses, one or more mirrors and/or a wavefront light source may be designed to be adjustable in their position. These further optical elements may also be supported at the assembly housing.

Thereby, all optical elements of the assembly may be adjusted with a required accuracy in an decoupled state from the microscope housing.

The beam splitter does not necessarily have to be arranged in the microscope beam path of the microscope during the coupling of the coupling opening and the coupling element. Rather, the beam splitter may be small enough, that a left and a right observation beam path of a stereo microscope may pass the beam splitter at a predetermined distance, wherein the left and the right observation beam path are configured to traverse the objective lens. The microscope beam path comprises the left and the right observation beam path.

According to an embodiment, the beam splitter is supported such that it is arranged in the microscope beam path of the microscope during the coupling of the coupling opening and the coupling element. Thereby, it is possible, that the beam splitter is designed such that an area of an projection of the beam splitter along an optical axis of the objective lens onto a plane, which is perpendicular to the optical axis of the objective lens amounts to at least 50%, in particular at least 70%, further in particular at least 90% of an area of a projection of the objective lens along the optical axis onto the plane. Thereby, a wavefront having a comparatively great cross-sectional extent may be characterized by the wavefront analysis system.

According to an embodiment, a plurality of lenses, in particular an eyepiece and/or a zoom system is supported at the housing of the microscope.

Thereby, it is for example possible to vary a magnification of the microscopical imaging. Furthermore, a semi-transparent mirror, an imaging optical system and a camera may be arranged in the microscope beam path, which may comprise a left and a right observation beam path.

According to an embodiment the wavefront analysis system comprises a wavefront light source for generating a wavefront measuring light and a wavefront light beam splitter for illuminating an object region with wavefront measuring light along a wavefront beam path. This is in particular the case during the coupling of the coupling opening and the coupling element. The wavefront measuring light, which is generated by the wavefront light source is reflected by the wavefront light beam splitter and reflected by the beam splitter. Thereafter, the wavefront measuring light leaves the assembly through the exit region of the assembly towards the object region. Thereafter, the wavefront measuring light may be incident on an object which is arranged in the object range. The object may for example be a human eye. The wavefront measuring light, which reaches the human eye may substantially have the shape of a plane wavefront. By transmitting the human cornea and the human lens, the substantially plane wavefronts are converted into substantially spherical convergent wavefronts, which are image onto a sharp illumination spot on the retina of the human eye. Depending on an ametropia of the eye, which is to be examined, this spot may for example be circular or ellipsoidal. Caused by a diffuse reflection at the retina, wavefront measuring light of a substantially spherical wavefront emanates from the illumination spot on the retina. The wavefront measuring light, which has a substantially spherical wavefront traverses the vitreous body, the human lens and the human cornea. After having left the eye, the wavefront measuring light is reflected at the beam splitter, which is arranged at the assembly and enters the wavefront analysis system. Depending on an ametropia of the eye, the shape of the wavefront of the wavefront measuring light deviates from the shape of a plane wavefront. These deviations may be measured by the wavefront analysis system for determining the optical properties of the eye, which is examined.

According to an embodiment, the wavefront measuring light comprises wave lengths of a near infrared wavelength range.

Wavelengths in the near infrared wavelengths range comprise wavelengths of between 700 nm and 1000 nm, in particular of between 750 nm and 850 nm, further in particular of about 850 nm. The wavefront light source may comprise a laser, a laser diode and/or a superluminescence diode (SLD).

According to an embodiment, the beam splitter which is arranged in the assembly comprises a dichroic beam splitter, which is configured such that a part of an intensity of the wavefront measuring light which is reflected is greater than a part of an intensity of the wavefront measuring light, which is transmitted.

The beam splitter may comprise a substrate, on which thin dielectric layers with a high and low refractive index are deposited, such as by vaporization deposition. The thickness and the numbers of the layers may be chosen such that, caused by interference, light of wavelengths which are comprised by the wavefront measuring light is reflected with a higher efficiency than transmitted.

According to an embodiment, the beam splitter is designed such that the wavefront measuring light is deflected by an angle of between 50° and 130°, in particular of between 70° and 110°, further in particular of between 80° and 100°, in particular by 90°, further in particular of between 70° and 150°, further in particular of between 90° and 130°, further in particular of between 100° and 120°, further in particular by 110°.

Further according to an embodiment, a smallest angle between a reflecting face of the beam splitter and an optical axis of the objective lens ($\delta$) may amount to 55°±5° or 45°±5°.

According to a further embodiment, the beam splitter is designed such that a part of a microscope imaging light for imaging the object region, which is transmitted, is greater than and a part of the microscope imaging light, which is reflected, wherein the microscope imaging light comprises wavelengths, which are different from the wavelengths of the wavefront measuring light.

Thereby, it is possible that a higher signal for the microscope image is obtained.

According to an embodiment, the objective lens comprises a plurality of component lenses. The component lenses may be supported in a fixed arrangement relative to each other, for example by holding elements and/or cement.

According to an embodiment, the beam splitter and the objective lens are arranged such that the wavefront beam path does not traverse a component lens of the plurality of component lenses of the objective lens during the coupling of the coupling opening and the coupling element.

According to an embodiment, the beam splitter and the objective lens are arranged such that the plurality of component lenses are arranged outside the wavefront beam path during the coupling of the coupling opening and the coupling element.

According to an embodiment, the beam splitter and the objective lens are arranged such that the wavefront beam path traverses at least one component lens of the plurality of component lenses of the objective lens during the coupling of the coupling opening and the coupling element.

According to an embodiment, the assembly comprises a protecting plate, which is arranged in the wavefront beam path between the beam splitter and the object region.

The protecting plate may be substantially transparent for the wavefront measuring light and the microscope imaging light. Thereby, the interior of the assembly may be protected from dust or dirt and all optical components which are contained in the assembly are reliably protected from contamination which may affect their functionality.

According to an embodiment, a smallest angle between the surface normal of the protecting plate and an optical axis of the objective lens is 15°±10°, in particular 15°±5°, further in particular 15°±3°.

Through such an angle formed between the protecting plate and the optical axis, it is possible, that reflections of wavefront measuring light or of illumination light of the microscope have no detrimental effects on the images of the microscope or the measurements of the wavefront analysis system.

According to an embodiment, the beam splitter and the objective lens are arranged such that the wavefront beam path traverses at least one component lens of the plurality of component lenses of the objective lens during the coupling of the coupling opening and the coupling element.

In such a case, the component lens of the objective lens, which is traversed by the wavefront beam path may be the optical component of the assembly and of the optical system, which is arranged closest to the object region.

In such case, a protecting plate may not be required, since the assembly may be already sealed for preventing penetration of dust or dirt into the assembly by the component lens, which is traversed by the wavefront beam path. The beam splitter may be arranged between component lenses of the objective lens, wherein at least one component lens may be arranged close to or at the coupling element. The component lens, which is traversed by the wavefront beam path may be arranged at the entry region of the assembly. The entry region of the assembly may comprise an opening in the assembly housing. Thereby, the component lens, which is traversed by the wavefront beam path may be designed such that it seals the opening of the entry region of the assembly.

According to an embodiment, the beam splitter and the objective lens are arranged such that the wavefront beam path traverses all component lenses of the plurality of component lenses of the objective lens during the coupling of the coupling opening and the coupling element. In other words, the wavefront beam may traverse all component lenses of the objective lens. For example, all component lenses of the objective lens in the wavefront beam path may be arranged between the beam splitter and the object region. Additionally, the component lenses may be designed such that they seal the opening of the entry region of the assembly.

Thereby, a protecting plate for sealing the assembly may not be necessary, since the assembly is already sealed by all component lenses of the objective lens in the entry region of the assembly.

According to an embodiment, the wavefront analysis system comprises a wavefront lens system for imaging the object region onto the array of microlenses during the coupling of the coupling opening and the coupling element.

The wavefront lens system may comprise at least two lenses, which are arranged in the wavefront beam path between the beam splitter and the array of microlenses. In particular, the two lenses may form a Kepler telescope. A Kepler telescope may be defined as a system which consists of two lenses, which are arranged at a distance from each other, wherein the distance amounts to the sum of the focal lengths of the two lenses. Such a Kepler telescope converts a bundle of parallel incident light beams into a bundle of parallel outgoing light beams. A size of a cross-section of the outgoing light bundle after being transmitted through the Kepler telescope may be increased or decreased compared to a cross-section of an incident light bundle. Thereby, it is possible, to adapt a cross-section of wavefront measuring light, which emanates from the object region to a cross-section, which corresponds to a size of the array of microlenses.

According to an embodiment, the coupling opening and the coupling element comprise a bayonet catch and/or a screw catch.

The coupling opening and/or the coupling element may comprise a thread such as a female thread or a male thread or a structure. The structure may be complementary in at least a portion thereof, to allow an engagement or a snap-in fastening. Furthermore, the coupling opening and/or the coupling element may comprise a locking element, such as a catch, or a pin, which is biased by a spring or the like. Thereby, a fast and simple mounting of the assembly to the microscope housing is possible.

According to an embodiment, the coupling opening and the coupling element may be designed such that a relative nominal position between the coupling opening and the coupling element, has a deviation by a shift of less than 2 mm, in particular less than 1 mm, in particular less than 0.5 mm.

According to a further embodiment, the coupling opening and the coupling element may be designed such that a tilt between the optical axis of the microscope housing and an optical axis of the objective lens is less than 3°, in particular less than 1°.

The optical axis of the microscope housing may be defined in particular by the zoom system and/or the eyepiece.

Thereby, no further adjustment operations are necessary after coupling opening has been coupled to the coupling element for performing optical microscopy and wavefront analysis with a correct alignment of the optical elements.

According to an embodiment, the optical system, which provides a microscope and a wavefront analysis system comprises an interchangeable objective lens with an interchange coupling element for the detachable coupling of the interchangeable objective lens to the coupling opening of the microscope housing.

The interchangeable objective lens may be designed such that the interchangeable objective lens is arranged in the microscope beam path of the microscope during the coupling of the coupling opening and the interchange coupling element wherein the assembly is dismounted from the housing of the microscope. Hence, the object region is arranged outside of the wavefront beam path.

Thereby, it is possible to provide an optical system only for optical microscopy by exchanging the assembly, which comprises the wavefront analysis system with the interchangeable objective lens through a coupling of the coupling opening and the interchange coupling element. Hence, the wavefront analysis system may be removed in case more space is needed for performing surgical operations.

Due to the possibility of coupling of the coupling opening and the interchange coupling element at a high precision, as described above, also in this operation mode of the optical system, no adjustment operations for the optical components are necessary for a correct operation. Moreover, in case also a wavefront measurement is needed, the interchangeable objective lens can be readily dismounted from the microscope housing. Thereafter, the assembly, which comprises the wavefront analysis system can be coupled to the microscope housing for continuing the examination or the surgery.

According to an embodiment, there is provided an assembly for a microscope having a microscope housing, wherein the assembly provides an assembly housing having a coupling element for a detachable coupling the assembly to a coupling opening of the microscope housing; an objective lens for imaging an object region; a wavefront analysis system, which provides a wavefront beam path; and a beam splitter, which is arranged in the wavefront beam path, wherein the objective lens, the beam splitter and the wavefront analysis system are arranged such that the object region is arranged in the wavefront beam path, wherein the coupling element comprises an objective lens frame, which surrounds and supports the objective lens.

The object region may for example be defined as a focal plane of the objective lens. The object region is arranged in the wavefront beam path. In other words, the object region is arranged such that wavefronts, which emanate from the object region or which traverse the object region are characterizable by the wavefront analysis system. In particular, an object plane in the object region may be an optically conjugate plane to the a detection plane of the wavefront sensor of the wavefront analysis system.

According to an embodiment, the smallest angle, which is formed by the reflecting face of the beam splitter and an optical axis of the objective lens, is 65°±5° or 55°±5° or 45°±5°. Thereby, wavefront measuring light, which propagates along the wavefront beam path, may be deflected by 130°±10° or 110°±10° or 90°±10°.

According to an embodiment, the assembly comprises a first lens group and a second lens group, wherein both lens groups are arranged in the wavefront beam path. Each of the first lens group and the second lens group may be formed by a plurality of component lenses, wherein the component lenses are supported in a fixed position relative to each other. For example, the first lens group and/or the second lens group may be designed as a cemented lens.

According to an embodiment, the assembly further comprises an array of microlenses, which is arranged in the wavefront beam path, wherein the first lens group and the second lens group are designed and arranged such that the object region is imaged onto the array of micro lenses.

According to an embodiment, the assembly further comprises at least one mirror, which is arranged between the first lens group and the second lens group. Also, more than one mirrors, in particular two mirrors, three mirrors of four mirrors may be arranged between the first lens group and the second lens group in the wavefront beam path.

Through the at least one mirror, which is arranged between the first lens group and the second lens group, it is possible to provide a wavefront beam path, which is folded within the assembly, such that the assembly has a compact design and requires only little space. Thereby, the assembly does not significantly reduce a the workspace, which is needed for performing surgical operations.

According to an embodiment, the assembly further comprises a third lens group, which is arranged between the second lens group and the array of microlenses.

According to an embodiment, an optical path of the wavefront beam path between the second lens group and the third lens group is adjustable.

By adjusting the optical path of the wavefront beam path between the second lens group and the third lens group, wavefront measuring light, which emanates from the object region, and which has spherical wavefronts, may be converted into measuring light having substantially plane wavefronts. Hence, by an adjusting the optical path between the second lens group and the third lens group, a compensation of the shape of the wavefront may be performed. Thereby, it is possible for example to examine eyes, which are strongly ametropic, without having to use a wavefront sensor with a high dynamic range.

According to an embodiment, there is provided an assembly for a microscope having a microscope housing, wherein the assembly comprises: an assembly housing with a coupling element for a detachable coupling of the assembly to a coupling opening of the microscope housing, wherein the coupling element comprises a coupling element axis; a wavefront analysis system having a wavefront light source for emitting wavefront measuring light; a beam splitter; wherein the wavefront light source and the beam splitter are arranged such that the wavefront measuring light is reflected such that the wavefront measuring light propagates substantially parallel to the coupling element axis; and wherein a smallest angle formed between a reflecting face of the beam splitter and the coupling element axis is 65°±5° or 55°±5°.

According to an embodiment, there is provided an assembly with a microscope housing, wherein the assembly comprises: an assembly housing with a coupling element for a detachable coupling of the assembly to a coupling opening of the microscope housing; a wavefront analysis system having a wavefront light source for emitting wavefront measuring light; a beam splitter; wherein the wavefront analysis system comprises an array of microlenses, which define optical axes of the array of microlenses; and wherein a smallest angle ( ) which is formed between a reflecting face of the beam splitter and one optical axis of the optical axes of the microlenses is 25°±5° or 35°±5°.

BRIEF DESCRIPTION OF THE DRAWINGS

The forgoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

FIG. 3 shows an assembly of an optical system according to an further embodiment;

FIG. 4A shows an optical system according to a further embodiment during an examination of an eye;

FIG. 4B shows an assembly of the optical system, which is illustrated in FIG. 4A according to an embodiment;

FIG. 5A shows an optical system according to a further embodiment during an examination of an eye; and FIG. 5B shows an assembly of the optical system, which is illustrated in FIG. 5A according to an embodiment.

DETAILED DESCRIPTION OF THE INVENTION

Figure 1A:
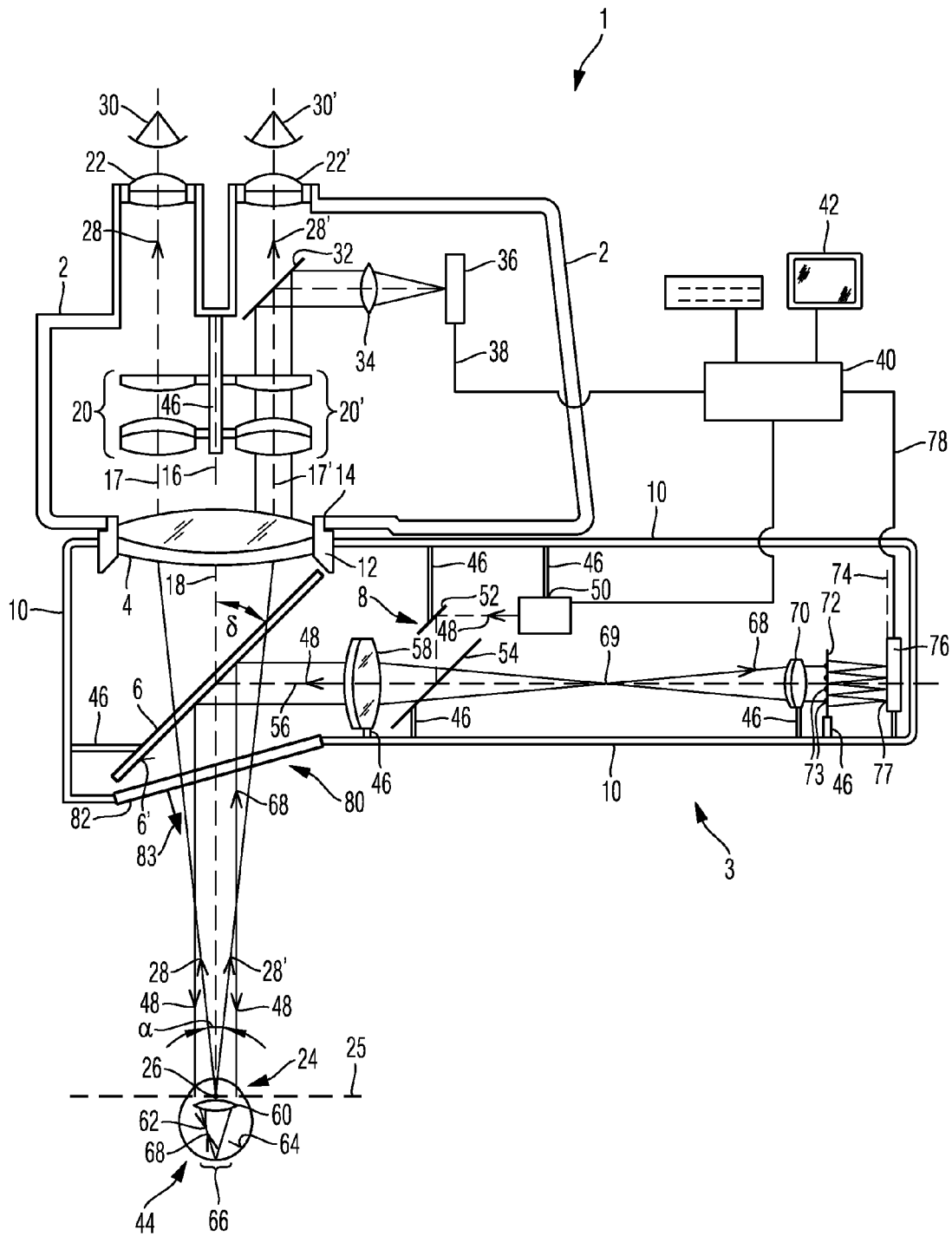
FIG. 1A shows an optical system according to an embodiment during an examination of an eye.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

FIG. 1A shows in a schematic representation an optical system 1 according to an embodiment. The optical system 1 comprises a microscope housing 2, in which a plurality of optical components are arranged, and an assembly 3 for wave front analysis, which comprises an objective lens 4, a dichroic beam splitter 6 and a wave front analysis system 8 as well as an assembly housing 10, which supports these elements. A smallest angle d which is formed between a reflecting face 6' of the beam splitter 6 and an optical axis 18 of the objective lens 4 amounts to about 45°±5°, in particular 55° and in other embodiments 55°±5°.

FIG. 1A shows the optical system 1 in an operation mode in which the wave front analysis module 3 with the microscope housing 2 is coupled by a coupling of the coupling element 12 of the wave front analysis module 3 with a coupling opening 14 of the microscope housing 2. In the embodiment shown in FIG. 1A, the coupling opening 14 is designed as a circular opening in the microscope housing 2 which comprises a female thread. In the illustrated embodiment, the coupling element 12 is designed as a circular ring having a male thread, which is screwed together with the coupling opening 14. Within the ring-shaped coupling element 12, the objective lens 4 is supported such that an adjustment of the position of the objective lens is possible by screws of the coupling element 12, which are not illustrated.

The objective lens 4 comprises a cemented lens which comprises two component lenses, which are arranged directly adjacent to each other. The objective lens is arranged by the coupling of the coupling opening 14 and the coupling element 12 such that the optical axis 18 of the object lens is co-linear to the optical axis 16 of the microscope housing, wherein the optical axis 16 of the microscope housing is located between the axes 17 and 17', which are defined by the zoom system 20 and the eyepiece 22 and by the zoom system 20' and the eyepiece 22'. The axes 17, 17' define a left and a right observation beam path of the stereo-microscope. In the coupled state of the wave front analysis module 3 with the microscope housing 2, which is illustrated in FIG. 1A, the object region 24 is located in the focal plane 25 of the objective lens 4. From the point 26 in the object region, which is illuminated by an illumination light source which is not illustrated, light beams 28 and 28' emanate, forming a stereo angle α. After having traversed the objective lens 4 at a distance from the optical axis 18 of the objective lens 4, the light beams 28 and 28' are converted into parallel beams 28 and 28'. The light beams 28 and 28' are separately guided through zoom systems 20 and 20' and through the eyepieces 22 and 22' for entering a left eye 30 and a right eye 30' of an observer. On the retina of the left eye and on the retina of the right eye, an image of the point 26 in the object region 24 is generated. Since the light beams 28 and 28' emanate from the point 26 in different directions, the observer has the impression of a stereoscopic image of the object region 24.

Optionally, within the microscope housing 2, there is arranged a semitransparent mirror 32 in the right observation beam path 28' between the zoom system 20' and the eyepiece 22' for reflecting a portion of the light 28'. The reflected portion is imaged onto a position sensitive detector 36 after having traversed an imaging optical system 34. This additional imaging mechanism may be omitted in another embodiment or designed differently. The detector 36 comprises a plurality of detector segments, which are arranged in a two-dimensional array. The position sensitive detector 36 may comprise for example a CMOS camera or a CCD camera, which comprises a plurality of light-sensitive pixels. Depending on an intensity of the detected light, the pixels generate electrical signals which are transmitted to a processing system 40 via a signal line 38. Processing system 40 is designed such that electrical signals are processed for displaying on the monitor 42 an image, representing detected light intensities. Alternatively or additionally, a microscope image of the object region 24 may be displayed on a head mounted display, which is not illustrated.

FIG. 1A shows an optical system, which is used for examining a human eye 44, arranged in the object region 24 of the focal plane 25 of the objective lens 4. The optical system 1 may be used for examining a human eye 44 before, during or after a surgery, in particular cataract surgery. In such a surgery, it is desirable to determine and measure optical properties of the human eye 44, in particular hyperopia, myopia and/or astigmatism. For this purpose, the wave front analysis module 3 is connected with the microscope housing 2 by a coupling of the coupling element 12 with the coupling opening 14.

The wave front analysis module 3 comprises an assembly housing 10, which supports through holding elements 46 the dichroic beam splitter 6 and the wave front analysis system 8. The holding elements 46 allow an adjustment of the respective positions of the components by adjustment mechanisms like adjustments screws which are not illustrated. The wave front analysis system 8 comprises a laser or a super luminescence diode (SLD) 50 for generating a wave front measuring light 48. The laser or the super luminescence diode 50 generates wave front measuring light 48, which comprises wavelengths in the range of about 750 nm to 850 nm. In particular, the SLD may generate wave front measuring light 48 having a spectral full width at half maximum of 50 nm. Wave front measuring light 48 is collimated by a collimator optical system and is reflected at the mirror 52. The wave front measuring light 48, which is reflected at the mirror 52 is reflected at the semi-transparent mirror 54, for traversing a lens 58 along the wave front beam path 56. Lens 58 transforms the wave front measuring light 48 into substantially parallel wave fronts. The wave front measuring light 48 is directed by the dichroic mirror 6, which reflects at least 70% of an intensity of the wave front measuring light 48, from the horizontal direction into the vertical direction by 90°. This is caused by the fact that the mirror surface 6' of the mirror 6 is arranged at an angle of 45° relative to the horizontal direction. Between the dichroic mirror 6 and the lens 58 the wave front beam path is oriented along the horizontal direction.

Dichroic mirror 6 is positioned by an adjustment of its position by means of adjustment screws, which are not illustrated, and held through an holding element 46. Thereby, it is possible to adjust a position of the dichroic mirror 6 such that the beam path 48 of the wave front measuring light 48 (i.e. along a propagation direction of the wave front measuring light 48, which comes from the wavefront light source, behind the dichroic mirror) is collinear to the optical axis of the objective lens 4. After the wave front measuring light 48 has been reflected at the dichroic mirror 6, substantially plane wave fronts 48 enter the human eye 44. The wave front measuring light 48 traverses the cornea of the human eye and the natural lens 60, whereby the wave front measuring light is refracted to form substantially convergent spherical wave fronts 62 downstream of the natural lens 60. The wave fronts 62 are converging at the retina 64 of the human eye 44 in region 66. The size and the shape of the region 66 depends on a hyperopia, myopia and/or astigmatism of the human eye 44. For an eye 44 without ametropia, a sharp point of wave front measuring light is formed in the region 66.

Through diffuse reflection, substantially spherical wave fronts 68 of the wave front measuring light emanate from the illuminated region 66 for forming substantially plane wave fronts of wave front measuring light after having traversed the natural lens 60 and the cornea 44. Wave front measuring light 68 which returns from the eye 44 is reflected by the dichroic mirror 6 and traverses the lens 58 along the wave front beam path 56. Lens 58 is a lens having positive optical refractive power, which transforms the wave front measuring light 68, which returns from the eye to substantially convergent spherical wavefronts. The convergent spherical wavefronts partially traverse the semi-transparent mirror 54 and are focused at a point 69 and further propagate downstream as spherical divergent wavefronts. At a distance of the lens 58, which corresponds to a sum of the focal length of the lens 58 and the focal lens of the lens 70, the lens 70 is arranged in the beam path 56 of the wavefront analysis system. The lens 70 transforms the divergent substantially spherical wavefront 68 into substantially plane wavefronts. The substantially plane wavefronts 68 traverse an array 72 of micro-lenses 73. In the focal plane 74 of the micro-lenses 73, there is arranged a position-sensitive detector which is a CCD camera 76 in this case. Each of the micro-lenses 73 in the array 72 of micro-lenses is traversed by a bundle of wavefront measuring light 68, which returns from the eye 44. Each bundle of wavefront measuring light 68 is imaged on a point 76 of the detector 76 which depends on a propagation direction of the bundle of wavefront measuring light 68. The position of the point 76 relative to the optical axis of the respective micro-lens 73 may be determined by processing with a processing system 40 the electrical signals which are generated by the detector 76. The output signals of the detector 76 are transmitted to the processing system 40 via signal line 78. From the positions, which are thereby obtained, information may be derived about a shape of the wavefront of the wavefront measuring light 68, which returns from the eye 44. From the such determined shape of the wavefront of the wavefront measuring light, optical properties of the eye 44 may be determined such as hyperopia, myopia and/or astigmatism of the eye 44.

The wavefront analysis module 3 is enclosed within an assembly housing 10 for preventing a contamination of the optical components of the wavefront analysis module 3. Through light entry region 80, the light 28 and 28', which is used for microscopic imaging enters the wavefront analysis module 3 and the wavefront measuring light 48 which is generated by the wavefront light source 50 exits and the wavefront measuring light 68, which returns from the eye 44, enters. In the light entry region 80, there is provided a protecting plate 82 which is made of a material, which is transparent in the visible and in the near infrared wavelength range and through which the wavefront analysis module 3 is sealed. A normal vector 83 of the protecting plate 82 and the optical axis 18 of the objective lens 4 form an angle of about 50°±3°. Thereby, wavefront measuring light 68, which emanates from the object region 24 and imaging light 28 and 28' of the microscope which is partially reflected at the protecting plate 82 is deflected such that it does not return to the object region and hence does not generate artifacts.

When the wavefront measurement is finished, the wavefront analysis module 3 may be readily dismounted from the microscope housing 2 by disengaging the screw catch by unscrewing the coupling opening 14 having a female thread and the circular coupling element 12 having a male thread. Thereafter, an interchangeable objective lens which is arranged at a coupling element which is not arranged at an assembly housing, may be coupled to the microscope housing 2 by screwing together the coupling element 12 of the interchangeable objective lens and the coupling opening 14. In doing this, the optical axis 18 of the interchangeable objective lens, is arranged collinear with the optical axis 16 of the microscope housing 2 such that the object region 24 is located in a focal plane of the interchangeable objective lens.

Figure 1B:
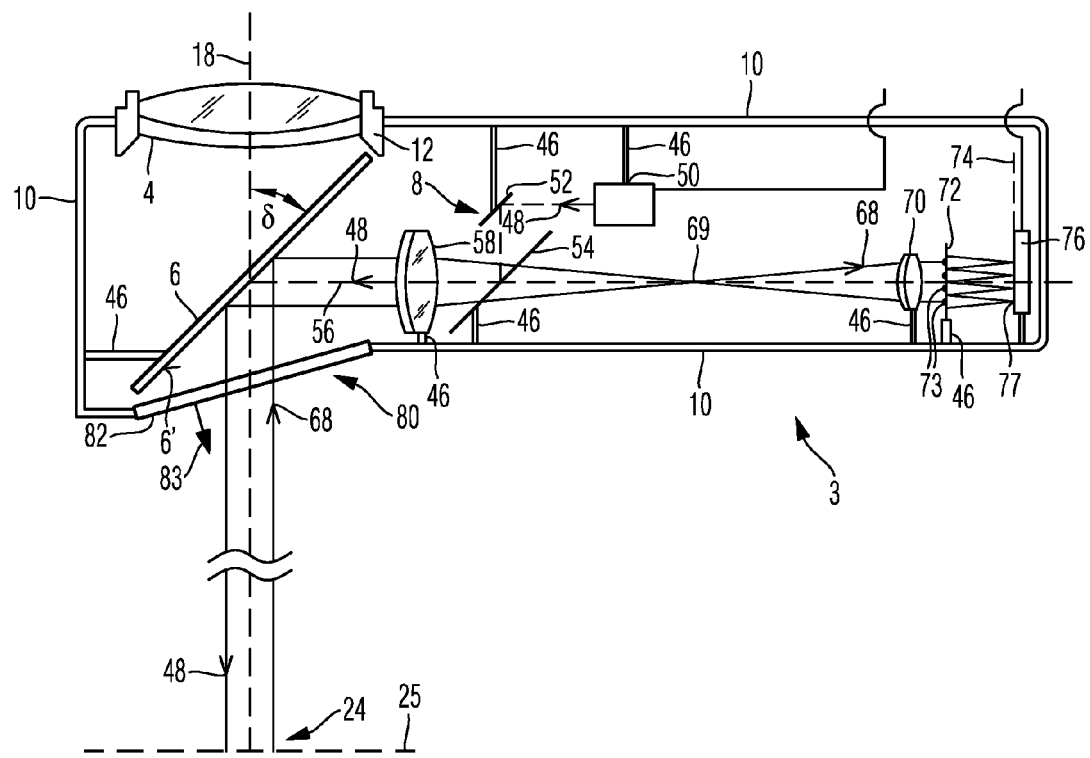
FIG. 1B shows an assembly of the optical system, which is illustrated in FIG. 1A according to an embodiment.

FIG. 1B shows a wavefront analysis module 3 in a state where it is dismounted from the microscope housing 2. The wavefront analysis module 3 may be separately used for analyzing wavefront measuring light 68 which emanates from or traverses the object region 24. For achieving this, the object region 24 is illuminated by use of a laser or a super luminescence diode 50 with wavefront measuring light 48 in a corresponding way as described above. The wavefront measuring light traverses the lens 58 and is reflected at the dichroic beam splitter 6 by an angle of 90° before illuminating the object region 24. A smallest angle between the reflecting face 6' of the dichroic beam splitter 6 and the optical axis 18 of the objective lens 4 is about 45°.

For coupling the wavefront analysis module 3 to the coupling opening 14, the coupling element 12 may be used. The coupling of the coupling element 12 and the coupling opening 14, which is shown in FIG. 1, may be performed directly or indirectly. For example, no further mechanical element for coupling the coupling element and the coupling opening is positioned between them. It is also conceivable that one or more adapter elements are positioned and/or fixed between the coupling element 12 and the coupling opening 14 during the coupling.

Figure 2A:
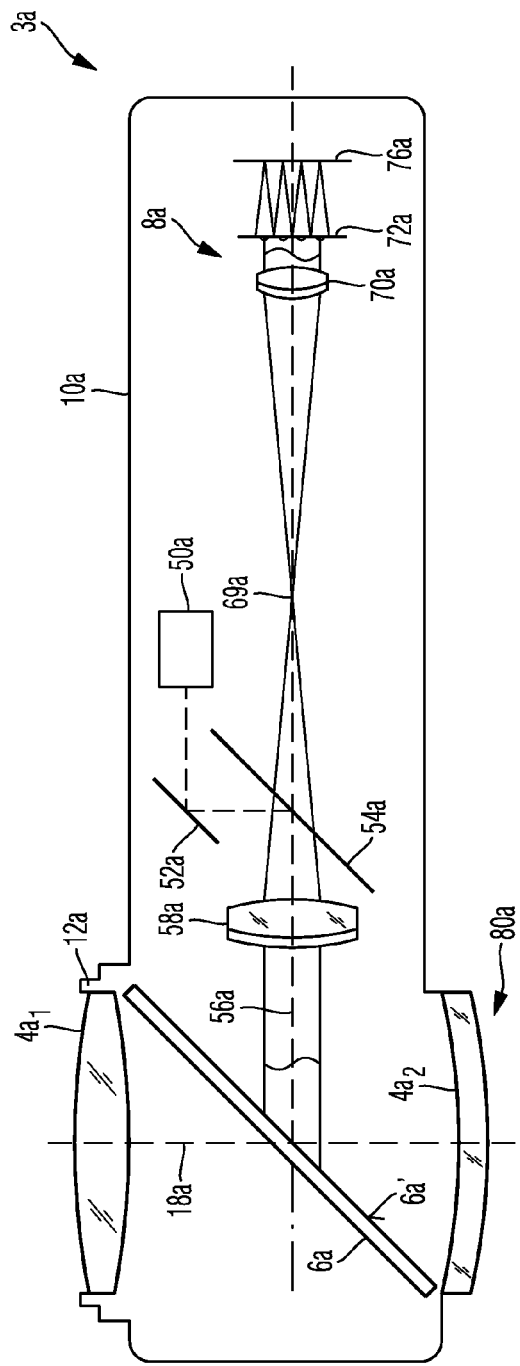
FIG. 2A shows an assembly of an optical system according to an embodiment.

FIG. 2A shows a wavefront analysis module 3a of an optical system according to an embodiment. The wavefront analysis system 8a is designed corresponding to the wavefront analysis system 8 which is shown in FIG. 1A. A difference between the embodiment of the wavefront analysis module 3a which is illustrated in FIG. 2A and the wavefront analysis module 3 which is illustrated in FIG. 1A is the design of the objective lens 4a and the arrangement of the beam splitter 6a relative to the objective lens 4a. The embodiment which is shown in FIG. 2A comprises two component lenses 4a1 and 4a2 which are arranged displaced from each other along their optical axes wherein the optical axes are collinear to each other. The two component lenses 4a1 and 4a2 are supported at the assembly housing 10. Between the component lenses 4a1 and 4a2, there is arranged the dichroic mirror 6a. The mirror face 6a' of the dichroic mirror 6a and the optical axis 18 of the component lenses 4a1 and 4a2 form an angle of 45°. In the embodiment of the wavefront analysis module 3a, which is illustrated in FIG. 2A a protecting plate which is comprised by the wavefront analysis module 3 and which is illustrated in FIG. 1A may be omitted, since the component lens 4a2 protects the wavefront analysis module 3 by sealing against penetration of dirt into the wavefront analysis module.

Figure 2B:
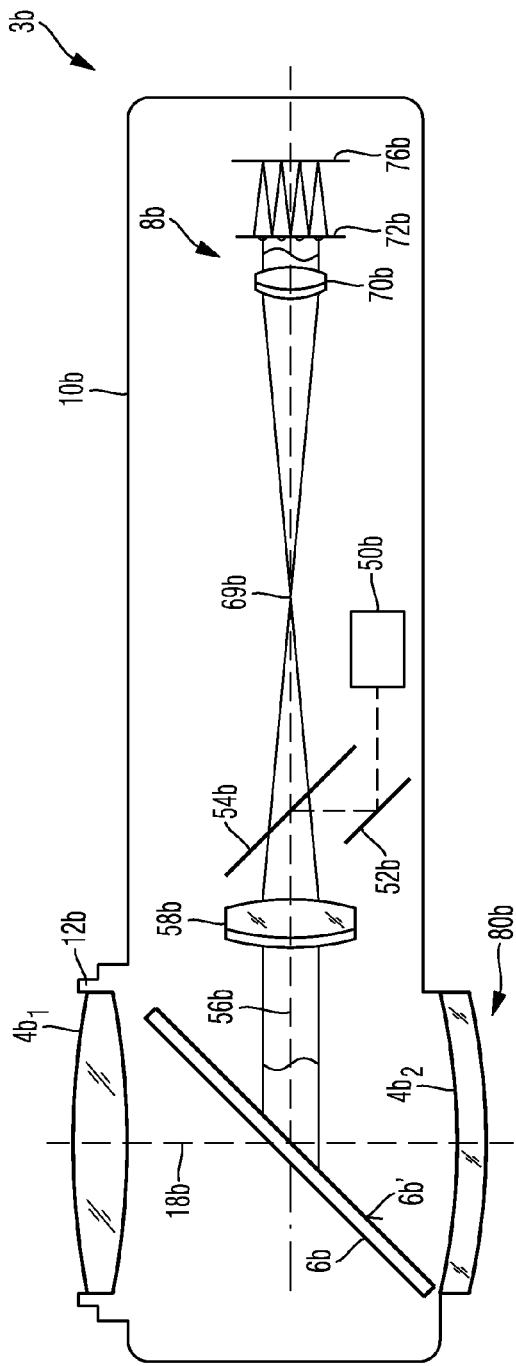
FIG. 2B shows an assembly of an optical system according to an embodiment.

FIG. 2B schematically illustrates a further embodiment of a wavefront analysis module 3 of an optical system according to an embodiment. The wavefront analysis module 3b which is illustrated in FIG. 2B corresponds to the embodiment of the wavefront analysis module 3a which is illustrated in FIG. 2A except for the arrangement of the wavefront light source 50b and the arrangement of the mirror 52b. The light source for the wavefront measuring light 50, 50a, 50b may be arranged at different positions within the wavefront analysis module 3, 3a and 3b for example in the views according to FIGS. 1, 2A, 2B above or beneath the lenses 58, 70 or 58a, 70a or 58b, 70b respectively. Alternatively, the light source of the wavefront measuring light 50, 50a, 50b may be arranged at any azimuthal position relative to the wavefront beam path 56, which is defined between the array 72, 72a, 72b of microlenses and the beam splitter 6, 6a, 6b by a horizontal axis. Thereby, also the position of the mirror 52, 52a, 52b and the semi-transparent mirror 54, 54a, 54b may be changed.

FIG. 3 illustrates a further embodiment of a wavefront analysis module of an optical system according to an embodiment. The embodiment which is schematically illustrated in FIG. 3 of a wavefront analysis module 3c corresponds to the embodiment of wavefront analysis module 3, 3a and 3b which is illustrated in FIGS. 1, 2A and 2B, except for the design and arrangement of the objective lens 4c. In the embodiments which are illustrated in FIGS. 1, 2A and 2B, at least one component lens of the objective lens 4, 4a, 4b is supported at the coupling element 14, 14a and 14b. Thereby, during a coupling of the coupling opening of the microscope housing and the coupling elements 12, 12a, 12b, at least a component lens of the objective lens 4, 4a, 4b is arranged close to or at the coupling opening 14, in particular in the microscope beam path between the zoom system 20, 20' and the beam splitter 6, 6a, 6b.

In contrast thereto, in the embodiment of a wavefront analysis module 3c which is shown in FIG. 3, the objective lens 4c is not supported at the coupling element 12c and not arranged during a coupling of the coupling opening 14 and the coupling element 12c between the zoom system 20, 20' and dichroic mirror 6c. The objective lens 4c is arranged beneath the dichroic mirror 6c, i.e. in the microscope beam path 18c between the dichroic mirror 6c and the object region 24c. Thereby, the optical refractive power of the objective lens 4c may be used completely for imaging the object region 24c onto the array 72c of the microlenses. Thereby, it is possible to reduce the optical power of the lenses 58c and 70c compared to the optical power of the lenses 58 and 70 (FIG. 1A), 58a and 70a (FIG. 2A), and 58b and 70b (FIG. 2B). The wavefront analysis module 3c which is illustrated in FIG. 3 is not completely sealed in a dismounted state from the microscope housing 2, since the ring-shaped coupling element 12c exposes a circular opening. This may entail penetration of dust or dirt. The wavefront analysis module 3c may be sealed in such a dismounted state by a not illustrated protecting cap, which has a female thread, which corresponds to the coupling opening 14.

FIG. 4A shows an optical system 1a according to a further embodiment, again during an examination of an eye 44. In the embodiment of the optical system 1a, which is schematically illustrated in FIG. 4A, the microscope housing 2a and the optical elements which are arranged in the microscope housing 2a are displayed only schematically and in a simplified way. The microscope which is formed within the microscope housing 2a with its optical elements may be designed similar to the stereo-microscope within the microscope housing 2 of FIG. 1A.

The assembly housing 10a spatially limits the wavefront analysis module 3a, wherein dichroic mirror 6a, a first lens group 58a, a second lens group 78 and a coupling element 12a and an objective lens 4a are supported at the assembly housing 10a by holding elements 46 which are not illustrated, corresponding to the embodiment which is illustrated in FIG. 1A.

Contrary to the embodiment of a wavefront analysis module 3 which is illustrated in FIG. 1A, a smallest angle which is formed between the reflecting face 6a' of the dichroic mirror 6a and the optical axis 18a of the objective lens 4a is not 45° but is greater and is 65°±5°, in particular 65°. Thereby, wavefront measuring light which emanates from the object region 24 within the focal plane 25 of the objective lens 4a or which traverses the object region 24 is deflected by an angle of about 130°. Such an inclination angle δ of the dichroic mirror 6a with respect to the optical axis 18a of the objective lens 4a allows a compact design of the wavefront analysis module 3a. The wavefront beam path 56a between the lenses 58a and 70a is not straight, such as the beam path 56 of the embodiment shown in FIG. 1A. Rather, the wavefront beam path is deflected two times by 110° or 90°, respectively, by additional mirrors 55 and 57 which are arranged in the wavefront beam path 56a between the lens 58a and the lens 70a. Thereby a multiply folded wavefront beam path 56a is provided which allows a compact design of the wavefront analysis module 3. Further elements, such as the wavefront light source 50a, the array 70a of microlenses 73a and detector 26a are designed as in the embodiment which is shown in FIG. 1A. However, wavefront light source 50a is arranged in a plane, which is different from the drawing layer of FIG. 4A and semi-transparent mirror 54a, which reflects the wavefront measuring light 48a which is generated by the wavefront light source 50a is not illustrated for the sake of simplicity.

FIG. 4B schematically illustrates the assembly 3a of the optical system, which is illustrated in FIG. 4A according to an embodiment. The assembly 3a is shown in FIG. 4B in a decoupled state from the microscope housing 2a. The assembly 3a, can be used separately for measurements. In doing this, wavefront analysis of wavefront measuring light, which emanates from an object region or traverses an object region may be performed as has been discussed in detail referring to FIG. 4A or FIG. 1A, respectively.

FIG. 5A shows an optical system 1d according to a further embodiment. Again, this embodiment is shown during an examination of an eye. In the schematically illustrated embodiment of FIG. 5A, the optical system 1d and the optical elements of the optical system 1d are only displayed in a schematic and simplified way. The microscope within the microscope housing 2d may be designed similar than the stereo-microscope within the microscope housing 2, which is schematically illustrated in FIG. 1A.

Contrary to the embodiments of an optical system, which have been illustrated so far, the objective lens 4d is supported in a separate frame 15, which comprises an external thread which may be screwed into a female thread of the coupling opening 14d of the microscope housing for arranging the objective lens 4d in the microscope beam path. In the embodiment which is illustrated in FIG. 5A, the objective lens 4d is not comprised by the wavefront analysis module 3d. The objective lens may be coupled to the microscope housing 2d by screwing together the coupling element 12d having a female thread and a male thread of the frame.

FIG. 5B schematically illustrates the assembly 3d of the optical system which is shown in FIG. 5A according to an embodiment in a decoupled state from the microscope housing 2d. The assembly 3d may be used separately for performing a wavefront analysis of wavefront measuring light, which emanates from or traverses the object region, as has been discussed in detail referring to FIG. 1, FIG. 4A or FIG. 1A.

The wavefront analysis module 3d is spatially limited by the assembly housing 10d which accommodates the dichroic mirror 6, a first lens group 58d, a second lens group 70d and a coupling element 12d. However, the assembly housing comprises no objective lens. The elements, which are accommodated in the assembly housing 10d are supported at the assembly housing 10d by holding elements 46 (not illustrated) in analogy to the embodiment, which is shown in FIG. 1A.

Unlike the embodiments of the wavefront analysis module, which have been described so far, the coupling element 12d comprises no frame for an objective lens and no objective lens is supported at the coupling element 12d. The coupling element forms a ring. An axis, which includes the center of the ring and which is oriented perpendicular to a plane, in which the ring is located, defines an axis of the coupling element.

A smallest angle which is formed between a reflecting face 6a' of the dichroic mirror 6a and the axis 19 of the coupling element amounts to 65°±5°, in particular 65° or 55°±5°, in particular 55°. Thereby, wavefront measuring light 68a which emanates from or traverses the object region is deflected by an angle of about 130° or 110°, respectively. Such an inclination angle δ of the dichroic mirror 6d with respect to the axis of the coupling element 19 enables a more compact design of the wavefront analysis module 3d.

Embodiments provide an assembly, which is coupleable to a microscope housing wherein the assembly comprises an objective lens and a wavefront analysis system, wherein an alignment of optical axes of a microscope beam path and a wavefront beam path by an adjustment of optical components within the assembly is possible, without requiring a further adjustment in case the assembly is coupled to the microscope housing. In doing this, also a focal plane of the objective lens and a focal plane of the imaging optical system of the wavefront analysis system are adjusted and aligned with respect to each other for allowing a microscopic imaging of the object region as well as an analysis of a wavefront which emanates from the object region.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. An optical system, comprising:
a microscope housing having a coupling opening for a detachable coupling of an objective lens of the optical system such that the objective lens is arranged in a microscope beam path of the optical system for imaging an object region of the objective lens; and
an assembly, which comprises
an assembly housing having a coupling element for the detachable coupling of the coupling element and the coupling opening of the microscope housing;
the objective lens;
a wavefront analysis system configured to analyze shapes of wavefronts that are emitted from an object, wherein the wavefront analysis system provides a wavefront beam path; and
a beam splitter, which is arranged in the wavefront beam path, wherein
the object lens, the beam splitter and wavefront analysis system are arranged such and the coupling element and the coupling opening are designed such that by the coupling of the coupling opening and the coupling element, the objective lens is arranged in the microscope beam path and the object region is arranged in the wavefront beam path, and further wherein
in a state in which the assembly is dismounted from the microscope housing, the object lens, the beam splitter and the wavefront analysis system are supported at the assembly housing.

2. The system according to claim 1, wherein the beam splitter is supported such that it is arranged in the microscope beam path by the coupling of the coupling opening and the coupling element.

3. The system according to claim 1, wherein in a state in which the assembly is dismounted from the microscope housing, a plurality of lenses, in particular at least one of an eyepiece or a zoom system is supported at the microscope housing in the microscope beam path.

4. The system according to claim 1, wherein the wavefront analysis system comprises a wavefront light source for generating a wavefront measuring light and a wavefront light beam splitter for illuminating the object region with the wavefront measuring light along the wavefront beam path.

5. The system according to claim 4, wherein the wavefront measuring light comprises wavelengths in a near infrared wavelength range.

6. The system according to claim1, wherein the beam splitter comprises a dichroic beam splitter wherein the beam splitter is designed such that a part of an intensity of the wavefront measuring light, which is reflected, is greater than a part of the intensity of the wavefront measuring light, which is transmitted.

7. The system according to claim 1, wherein the beam splitter is designed such that the wavefront measuring light is deflected by an angle of between 50° and 130°.

8. The system according to claim 1, wherein the beam splitter is designed such that a part of a microscope imaging light for imaging the object region, which is transmitted, is greater than and a part of the microscope imaging light, which is reflected, wherein the microscope imaging light comprises wavelengths, which are different from the wavelengths of the wavefront measuring light.

9. The system according to claim 1, wherein the objective lens comprises a plurality of component lenses.

10. The system according to claim 9, wherein the beam splitter and the objective lens are arranged such that the plurality lenses are arranged outside the wavefront beam path during the coupling of the coupling opening and the coupling element.

11. The system according to claim 9, wherein the beam splitter and the objective lens are arranged such that the wavefront beam path traverses at least one component lens of the plurality of component lenses of the objective lens during the coupling of the coupling opening and the coupling element.

12. The system according to claim 11, wherein the beam splitter and the objective lens are arranged such that the wavefront beam path traverses all component lenses of the plurality of component lenses of the objective lens during the coupling of the coupling opening and the coupling element.

13. The system according to claim 11, wherein
at least one further of the plurality of component lenses is arranged outside the wavefront beam path.

14. The system according to claim 9, wherein
the beam splitter is arranged in the microscope beam path between two of the plurality of component lenses.

15. The system according to claim 1, wherein the assembly comprises a protecting plate, which is arranged between the beam splitter and the object region, wherein
the protecting plate is substantially transparent for wavefront measuring light generated by a wavefront light source of the wavefront analysis system and for microscope imaging light for imaging the object region by using the imaging beam path.

16. The system according to claim 15, wherein a smallest angle between the surface normal of the protecting plate and an optical axis of the objective lens is 15°±10°.

17. The system according to claim 1, wherein the wavefront analysis system comprises a wavefront lens system and an array of microlenses for imaging an object region onto the array of microlenses during the coupling of the coupling opening and the coupling element.

18. The system according to claim 1, wherein the coupling opening and the coupling element comprise at least one of a bayonet catch or a screw catch.

19. The system according to claim 1, further comprising an interchangeable objective lens having a interchange coupling element for a detachable coupling of the interchangeable objective lens to the coupling opening of the microscope housing.

20. The optical system of claim 1, wherein
the objective lens, the beam splitter and the wavefront analysis system are adjustable in their position relative to each other.

21. The optical system of claim 1, wherein
the wavefront analysis system comprises a wavefront sensor.

22. The optical system of claim 1, wherein
the wavefront analysis system is configured to measure optical properties of an eye by the analyzing of the shapes of the wavefronts.

23. The optical system of claim 1, wherein
the coupling element comprises an objective lens frame, which surrounds and supports the objective lens.

24. The optical system of claim 1, wherein
a structure of the coupling opening is complementary to a structure of the coupling element, such that the coupling opening and the coupling element are detachably engageable with each other.

25. An assembly for a microscope having a microscope housing, wherein the assembly comprises:
an assembly housing having a coupling element for a detachable coupling of the assembly to a coupling opening of the microscope housing;
an objective lens for imaging an object region; and
a wavefront analysis system configured to analyze shapes of wavefronts that are emitted from an object, and wherein the wavefront analysis system further provides a wavefront beam path, wherein
by the coupling of the assembly to the coupling opening the objective lens and the wavefront analysis system are arranged such that the object region is arranged in the wavefront beam path, and wherein
in a state in which the assembly is dismounted from the microscope housing, the wavefront analysis system and the objective lens are supported at the assembly housing, and further wherein
the coupling element comprises an objective lens frame, which surrounds and supports the objective lens.

26. The assembly according to claim 25, further comprising a beam splitter, which is arranged in the wavefront beam path between the object region and the wavefront analysis system.

27. The assembly according to claim 25, wherein a smallest angle between a reflecting face of the beam splitter and an optical axis of the objective lens is 65°±5° or 55°±5°.

28. The assembly according to claim 25, further comprising a first lens group and a second lens group, each of which are arranged in the wavefront beam path.

29. The assembly according to claim 28, further comprising an array of microlenses, which is arranged in the wavefront beam path, wherein the first lens group and the second lens group are designed such and arranged such that the object region is imaged onto the array of microlenses.

30. The assembly according to claim 29, further comprising a third lens group, which is arranged between the second lens group and the array of microlenses.

31. The assembly according to claim 30, wherein an optical path of the wavefront beam path between the second lens group and the third lens group is adjustable.

32. The assembly according to claim 28, further comprising at least one mirror, which is arranged in the wavefront beam path between the first lens group and the second lens group.

33. The optical system of claim 25, wherein
the wavefront analysis system comprises a wavefront sensor.

34. The optical system of claim 25, wherein
the wavefront analysis system is configured to measure optical properties of an eye by the analyzing of the shapes of the wavefronts.

35. The optical system of claim 25, wherein
a structure of the coupling opening is complementary to a structure of the coupling element, such that the coupling opening and the coupling element are detachably engageable with each other.

36. An assembly for a microscope having a microscope housing, wherein the assembly comprises:
an assembly housing having a coupling element for a detachable coupling of the assembly to a coupling opening of the microscope housing, wherein the coupling element comprises a coupling element axis;
a wavefront analysis system configured to analyze shapes of wavefronts that are emitted from an object, wherein the wavefront analysis system has a wavefront light source for emitting wavefront measuring light; and
a beam splitter, wherein
the wavefront light source and the beam splitter are arranged such that the wavefront measuring light is reflected such that the wavefront measuring light propagates substantially parallel to the coupling element axis, and further wherein
a smallest angle formed between a reflecting face of the beam splitter and the coupling element axis is 65°±5°, or 55°±5°.

37. The optical system of claim 36, wherein
the wavefront analysis system comprises a wavefront sensor.

38. The optical system of claim 36, wherein
wavefront analysis system is configured to measure optical properties of an eye by the analyzing of the shapes of the wavefronts.

39. The optical system of claim 36, wherein
in a state, in which the assembly is dismounted from the microscope housing, the wavefront analysis system and the beam splitter are supported at the assembly housing.

40. The optical system of claim 39, wherein
by the coupling of the coupling element and the coupling opening, an object region imaged by the microscope is arranged in a wavefront beam path provided by the wavefront analysis system.

41. The optical system of claim 36, wherein the assembly further comprises:
an objective lens for imaging an object region with a microscope beam path of the microscope, and wherein
the coupling element comprises an objective lens frame, which surrounds and supports the objective lens.

42. The optical system of claim 36, wherein the wavefront analysis system comprises:
an array of microlenses, which define optical axes of the array of microlenses; and wherein
a smallest angle which is formed between the reflecting face of the beam splitter and one of the optical axes of the microlenses is 25°±5° or 35°±5°.

43. The optical system of claim 36, wherein
a structure of the coupling opening is complementary to a structure of the coupling element, such that the coupling opening and the coupling element are detachably engageable with each other.

44. An assembly with a microscope housing, wherein the assembly comprises:
an assembly housing having a coupling element for a detachable coupling of the assembly to a coupling opening of the microscope housing;
a wavefront analysis system configured to analyze shapes of wavefronts that are emitted from an object, wherein the wavefront analysis system has a wavefront light source for emitting wavefront measuring light; and
a beam splitter, wherein
the wavefront analysis system comprises an array of microlenses, which define optical axes of the array of microlenses, and further wherein
a smallest angle which is formed between a reflecting face of the beam splitter and one optical axis of the optical axes of the microlenses is 25°±5° or 35°±5°.

45. The optical system of claim 44, wherein the wavefront analysis system comprises:
   a wavefront sensor.

46. The optical system of claim 44, wherein
   the wavefront analysis system is configured to measure optical properties of an eye by the analyzing of the shapes of the wavefronts.

47. The optical system of claim 44, wherein
   in a state, in which the assembly is dismounted from the microscope housing, the wavefront analysis system and the beam splitter are supported at the assembly housing.

48. The optical system of claim 47, wherein
   by the coupling of the coupling element and the coupling opening, an object region imaged by the microscope is arranged in a wavefront beam path provided by the wavefront analysis system.

49. The optical system of claim 44, wherein the assembly further comprises:
   an objective lens for imaging an object region with a microscope beam path of the microscope, and wherein
      the coupling element comprises an objective lens frame, which surrounds and supports the objective lens.

50. The optical system of claim 44, wherein
   a structure of the coupling opening is complementary to a structure of the coupling element, such that the coupling opening and the coupling element are detachably engageable with each other.

* * * * *